United States Patent
Geilich et al.

(10) Patent No.: US 12,115,055 B2
(45) Date of Patent: Oct. 15, 2024

(54) ABSORBENT ARTICLE WITH IMPROVED BONDING

(71) Applicant: The Procter & Gamble Company, Cincinnati, OH (US)

(72) Inventors: Ralf Geilich, Eppstein (DE); Vito Carla, Fairfield, OH (US); Digvijay Rawat, Cincinnati, OH (US); Ronda Lynn Glassmeyer, Cincinnati, OH (US); Pietro Cecchetto, Fairfield, OH (US); Christopher Philip Bewick-Sonntag, Cincinnati, OH (US); Christian Seib, Bad Friedrichshall (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/896,123

(22) Filed: Aug. 26, 2022

(65) Prior Publication Data

US 2022/0401274 A1     Dec. 22, 2022

Related U.S. Application Data

(63) Continuation of application No. 15/347,420, filed on Nov. 9, 2016, now Pat. No. 11,446,187, which is a
(Continued)

(51) Int. Cl.
*A61F 13/15* (2006.01)
*A61F 13/47* (2006.01)
(Continued)

(52) U.S. Cl.
CPC ............ *A61F 13/539* (2013.01); *A61F 13/47* (2013.01); *A61F 13/5116* (2013.01);
(Continued)

(58) Field of Classification Search
CPC .. A61F 13/539; A61F 13/47; A61F 13/53747; A61F 13/15699; A61F 13/537;
(Continued)

(56) References Cited

U.S. PATENT DOCUMENTS 3,929,135 A    12/1975  Thompson
4,076,663 A     2/1978  Masuda et al.
(Continued)

FOREIGN PATENT DOCUMENTS

CA    1280682 C    2/1991
CN    1774225 A    5/2006
(Continued)

OTHER PUBLICATIONS

All Office Actions, U.S. Appl. No. 13/310,271, filed Dec. 2, 2011.
(Continued)

*Primary Examiner* — Jacqueline F Stephens
(74) *Attorney, Agent, or Firm* — Amanda Herman Berghauer; Sarah M. DeCristofaro

(57) ABSTRACT

An absorbent article is provided. The absorbent article includes a liquid pervious film topsheet having a body facing surface and a garment facing surface; a backsheet having a body facing surface and a garment facing surface; an absorbent core having a body facing surface and a garment facing surface, the absorbent core being provided between the topsheet and the backsheet; and a bonding layer having a body facing surface and a garment facing surface. The body facing surface of the bonding layer has a fibrous matrix comprising cellulosic fibers and thermoplastic fibers, and the garment facing surface of the topsheet is directly bonded to the body facing surface of the bonding layer at discrete adhesive-free bond points.

20 Claims, 3 Drawing Sheets

Related U.S. Application Data continuation of application No. 13/310,271, filed on Dec. 2, 2011, now Pat. No. 9,504,613.

(60) Provisional application No. 61/418,943, filed on Dec. 2, 2010.

(51) Int. Cl.
  *A61F 13/511*  (2006.01)
  *A61F 13/537*  (2006.01)
  *A61F 13/539*  (2006.01)
  *A61F 13/53*   (2006.01)

(52) U.S. Cl.
  CPC .. *A61F 13/53747* (2013.01); *A61F 13/15699* (2013.01); *A61F 2013/4708* (2013.01); *A61F 2013/51173* (2013.01); *A61F 2013/51178* (2013.01); *A61F 2013/51182* (2013.01); *A61F 2013/530481* (2013.01); *A61F 13/537* (2013.01); *A61F 13/53708* (2013.01); *A61F 2013/5395* (2013.01)

(58) Field of Classification Search
  CPC ........ A61F 13/53708; A61F 2013/4708; A61F 2013/51173; A61F 2013/51178; A61F 2013/51182; A61F 2013/530481; A61F 2013/5395
  See application file for complete search history.

(56) References Cited

U.S. PATENT DOCUMENTS

| | | |
|---|---|---|
| 4,157,724 A | 6/1979 | Persson |
| 4,264,289 A | 4/1981 | Day |
| 4,278,113 A | 7/1981 | Persson |
| 4,321,924 A | 3/1982 | Ahr |
| 4,324,246 A | 4/1982 | Mullane et al. |
| 4,342,314 A | 8/1982 | Radel et al. |
| 4,352,649 A | 10/1982 | Jacobsen et al. |
| 4,353,687 A | 10/1982 | Nielsen |
| 4,425,130 A | 1/1984 | Desmarais |
| 4,463,045 A | 7/1984 | Ahr |
| 4,494,278 A | 1/1985 | Kroyer et al. |
| 4,589,876 A | 5/1986 | Van Tilburg |
| 4,609,518 A | 9/1986 | Curro et al. |
| 4,610,678 A | 9/1986 | Weisman et al. |
| 4,627,806 A | 12/1986 | Johnson |
| 4,629,643 A | 12/1986 | Curro |
| 4,640,810 A | 2/1987 | Laursen et al. |
| 4,650,409 A | 3/1987 | Nistri et al. |
| 4,654,039 A | 3/1987 | Brandt et al. |
| 4,724,980 A | 2/1988 | Farley |
| 4,726,976 A | 2/1988 | Karami et al. |
| 4,854,984 A | 8/1989 | Ball |
| 4,950,264 A | 8/1990 | Osborn, III |
| 5,006,394 A | 4/1991 | Baird |
| 5,009,653 A | 4/1991 | Osborn, III |
| 5,102,597 A | 4/1992 | Berg et al. |
| 5,342,338 A | 8/1994 | Roe |
| 5,374,260 A | 12/1994 | Lemay et al. |
| 5,466,232 A | 11/1995 | Cadieux et al. |
| 5,549,589 A | 8/1996 | Horney et al. |
| 5,607,414 A * | 3/1997 | Richards ............... A61F 13/539 604/370 |
| 5,897,541 A | 4/1999 | Uitenbroek et al. |
| 7,056,404 B2 | 6/2006 | Mcfall et al. |
| 7,102,054 B1 | 9/2006 | Cree |
| 7,172,801 B2 | 2/2007 | Hoying et al. |
| 7,270,861 B2 | 9/2007 | Broering et al. |
| 7,410,683 B2 | 8/2008 | Curro et al. |
| 7,507,459 B2 | 3/2009 | Turner et al. |
| 7,521,588 B2 | 4/2009 | Stone |
| 7,553,532 B2 | 6/2009 | Turner et al. |
| 7,648,752 B2 | 1/2010 | Hoying et al. |
| 7,655,176 B2 | 2/2010 | Stone et al. |
| 7,670,665 B2 | 3/2010 | Hoying et al. |
| 7,674,949 B2 | 3/2010 | Wahlström et al. |
| 7,682,686 B2 | 3/2010 | Curro et al. |
| 7,718,243 B2 | 5/2010 | Curro et al. |
| 8,043,984 B2 | 10/2011 | Stadelman et al. |
| 8,461,411 B2 | 6/2013 | Digiacomantonio et al. |
| 9,456,932 B2 | 10/2016 | Digiacomantonio et al. |
| 9,504,613 B2 | 11/2016 | Geilich et al. |
| 9,655,791 B2 | 5/2017 | Rawat et al. |
| 9,675,500 B2 | 6/2017 | Rawat et al. |
| 10,143,602 B2 | 12/2018 | Rawat et al. |
| 10,849,801 B2 | 12/2020 | Rawat et al. |
| 2003/0134094 A1 | 7/2003 | Zafiroglu et al. |
| 2004/0121120 A1 | 6/2004 | Gray |
| 2004/0122395 A1 | 6/2004 | Stone et al. |
| 2005/0087292 A1 | 4/2005 | Mcfall et al. |
| 2005/0170729 A1 | 8/2005 | Stadelman et al. |
| 2005/0281976 A1 | 12/2005 | Curro et al. |
| 2005/0283129 A1 | 12/2005 | Hammons |
| 2006/0229579 A1 | 10/2006 | Wahlström et al. |
| 2008/0119807 A1 | 5/2008 | Curro et al. |
| 2009/0030390 A1 | 1/2009 | Hammons |
| 2009/0030391 A1 | 1/2009 | Hammons et al. |
| 2010/0130952 A1* | 5/2010 | Murai ............... A61F 13/495 604/385.24 |
| 2010/0151170 A1 | 6/2010 | Thomas et al. |
| 2010/0230857 A1 | 9/2010 | Muhs et al. |
| 2010/0230858 A1 | 9/2010 | Stone et al. |
| 2010/0230866 A1 | 9/2010 | Gray |
| 2010/0230867 A1 | 9/2010 | Gray et al. |
| 2012/0157950 A1 | 6/2012 | Geilich et al. |
| 2012/0231238 A1 | 9/2012 | Rawat et al. |
| 2013/0316135 A1 | 11/2013 | Rawat et al. |
| 2017/0056258 A1 | 3/2017 | Geilich et al. |
| 2017/0216107 A1 | 8/2017 | Rawat et al. |
| 2019/0070047 A1 | 3/2019 | Rawat et al. |

FOREIGN PATENT DOCUMENTS

| | | |
|---|---|---|
| CN | 1902047 A | 1/2007 |
| EP | 0014501 A1 | 8/1980 |
| EP | 0395476 A2 | 10/1990 |
| EP | 0596532 A1 | 5/1994 |
| EP | 1295711 A1 | 3/2003 |
| EP | 2196176 A2 | 6/2010 |
| EP | 2645977 A1 | 10/2013 |
| GB | 2142276 A | 1/1985 |
| JP | H08511443 A | 12/1996 |
| JP | H09503944 A | 4/1997 |
| JP | 2003275239 A | 9/2003 |
| JP | 2004298454 A | 10/2004 |
| JP | 2005502509 A | 1/2005 |
| JP | 2005097782 A | 4/2005 |
| JP | 2006514849 A | 5/2006 |
| KR | 20010108479 A | 12/2001 |
| KR | 100754546 B1 | 9/2007 |
| KR | 20100040729 A | 4/2010 |
| RU | 2188039 C2 | 8/2002 |
| RU | 2197934 C2 | 2/2003 |
| RU | 2235559 C2 | 9/2004 |
| RU | 2395264 C2 | 7/2010 |
| WO | 9311725 A1 | 6/1993 |
| WO | 9311726 A1 | 6/1993 |
| WO | 9428843 A1 | 12/1994 |
| WO | 0059438 A1 | 10/2000 |
| WO | 2004108037 A1 | 12/2004 |
| WO | 2006093457 A1 | 9/2006 |
| WO | 2007069967 A1 | 6/2007 |
| WO | 2008146541 A1 | 12/2008 |
| WO | 2010104996 A1 | 9/2010 |
| WO | 2011118473 A1 | 9/2011 |
| WO | 2012044656 A1 | 4/2012 |

OTHER PUBLICATIONS

All Office Actions, U.S. Appl. No. 15/347,420, filed Nov. 9, 2016.
All Office Actions, U.S. Appl. No. 15/493,585, filed Apr. 21, 2017.

(56) References Cited

OTHER PUBLICATIONS

All Office Actions, U.S. Appl. No. 16/178,673, filed Nov. 2, 2018.
All Office Actions, U.S. Appl. No. 13/426,049, filed Mar. 21, 2012.
All Office Actions, U.S. Appl. No. 13/952,335, filed Jul. 26, 2013.
PCT Search Report and Written Opinion for PCT/US2011/062829 dated Mar. 14, 2012, 4 pages.

* cited by examiner

ABSORBENT ARTICLE WITH IMPROVED BONDING

CROSS REFERENCE TO RELATED APPLICATION

This application claims the benefit of U.S. Provisional Application No. 61/418,943 filed Dec. 2, 2010.

FIELD OF THE INVENTION

The invention relates to an article having improved bonding of a topsheet material to an absorbent material. More particularly, this invention relates to an article having improved bonding of a topsheet material to an absorbent material such that detachment or tearing of the topsheet during normal use of the article can be prevented.

BACKGROUND OF THE INVENTION

Absorbent articles such as sanitary napkins, pantiliners, tampons, absorbent interlabial devices, disposable diapers, incontinence products, and bandages are designed to absorb and retain liquid and other discharges from the human body and to prevent body and clothing soiling. In the manufacture of absorbent articles, it is generally necessary to bond the components that will form the absorbent article together in order to form the finished product. For example, topsheet materials can be bonded to an absorbent layer, such as, for example, a secondary layer, to provide added strength and reinforcement to the topsheet material.

Some topsheet materials, such as low cost soft and silky tactile topsheet materials, have weak material strength in the cross direction. It has been observed that using typical bonding methods, such as, for example, fusion bonding, to bond such materials to an absorbent layer can result in destruction of the material and compromised bond site integrity. One solution for bonding these types of materials includes adding glue to the bond sites; however, gluing the layers together results in a stiffer, less comfortable and more integrated laminate of materials. Thus, there remains a desire and need in the art to develop an article having sufficient bonding between the topsheet and the absorbent material, particularly when using a low cost topsheet material with weak material strength in the cross direction, so as to prevent tearing of the topsheet during use, without undesirably increasing the stiffness of the article.

SUMMARY OF THE INVENTION

An absorbent article is provided. The absorbent article includes a liquid pervious film topsheet having a body facing surface and a garment facing surface; a backsheet having a body facing surface and a garment facing surface; an absorbent core having a body facing surface and a garment facing surface, the absorbent core being provided between the topsheet and the backsheet; and a bonding layer having a body facing surface and a garment facing surface. The body facing surface of the bonding layer has a fibrous matrix comprising cellulosic fibers and thermoplastic fibers, and the garment facing surface of the topsheet is directly bonded to the body facing surface of the bonding layer at discrete adhesive-free bond points.

Also provided is an absorbent article comprising a liquid pervious film topsheet having a body facing surface and a garment facing surface; a backsheet having a body facing surface and a garment facing surface; and an absorbent core having a body facing surface and a garment facing surface, the absorbent core being provided between the topsheet and the backsheet; and a bonding layer having a body facing surface and a garment facing surface. The body facing surface of the bonding layer has a fibrous matrix comprising cellulosic fibers and thermoplastic fibers and the garment facing surface of the bonding layer is different from the body facing surface of the bonding layer. The garment facing surface of the topsheet is directly bonded to the body facing surface of the bonding layer at discrete bond points.

Further provided is an absorbent article comprising a liquid pervious film topsheet having a body facing surface and a garment facing surface, the topsheet comprising a plurality of discrete protruded extensions extending only from a first surface of the precursor web and macroapertures; a backsheet having a body facing surface and a garment facing surface; an absorbent core having a body facing surface and a garment facing surface, the absorbent core being provided between the topsheet and the backsheet; and a bonding layer having a body facing surface and a garment facing surface. The body facing surface of the bonding layer has a fibrous matrix comprising cellulosic fibers and thermoplastic fibers. The garment facing surface of the topsheet is directly bonded to the body facing surface of the bonding layer at discrete adhesive-free bond points.

DETAILED DESCRIPTION OF THE INVENTION

An absorbent article comprising a topsheet, such as, for example, a low cost soft and silky tactile topsheet, a bonding layer, and an absorbent core is provided. The bonding layer includes a fibrous matrix comprising cellulosic and thermoplastic fibers that is in intimate contact with and directly bonded to the topsheet. This configuration surprisingly results in an article having improved bonding between the topsheet and the bonding layer, without undesirably increasing the stiffness of the article.

The invention can be used in a variety of disposable absorbent articles, but is particularly useful in feminine hygiene products such as sanitary napkins and pantiliners. Embodiments of a disposable absorbent article that uses the invention are the sanitary napkins 10 shown in FIG. 1, FIG. 2, FIG. 3, and FIG. 4.

The illustrated sanitary napkin 10 has a body-facing upper side 11 that contacts the user's body during use. The opposite, garment-facing lower side 13 contacts the user's clothing during use.

Figure 1:
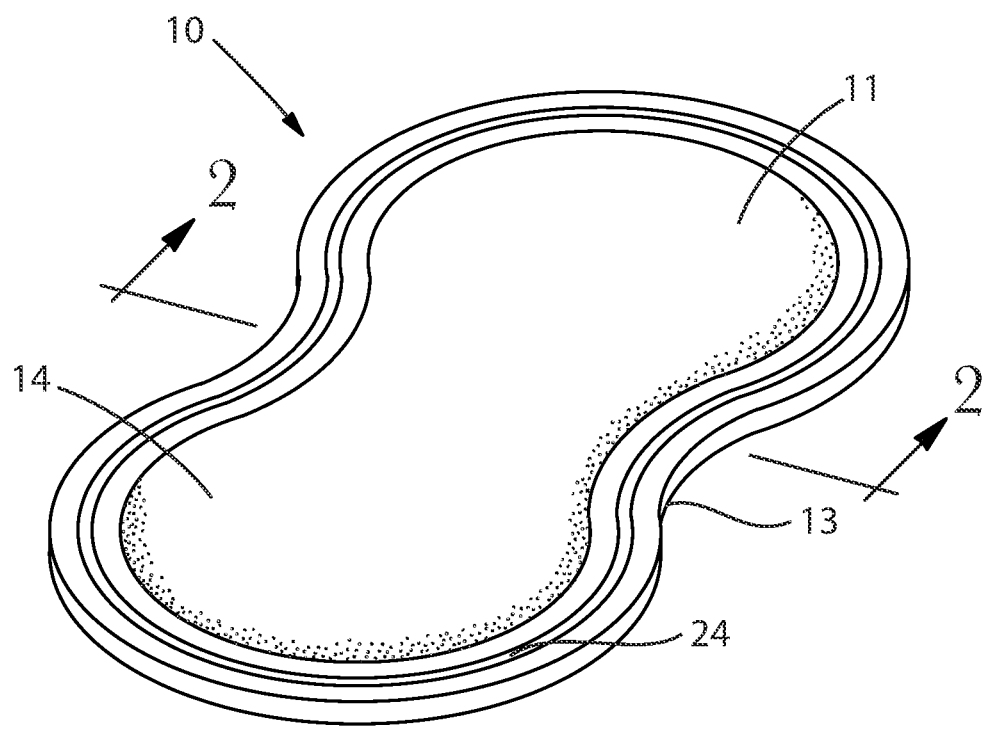
FIG. 1 is a perspective view of one embodiment of a sanitary napkin.

A sanitary napkin 10 can have any shape known in the art for feminine hygiene articles, including the generally symmetric "hourglass" shape as shown in FIG. 1, as well as pear shapes, bicycle-seat shapes, trapezoidal shapes, wedge shapes or other shapes that have one end wider than the other. Sanitary napkins and pantyliners can also be provided with lateral extensions known in the art as "flaps" or "wings" 15. Such extensions can serve a number of purposes, including, but not limited to, protecting the wearer's panties from soiling and keeping the sanitary napkin secured in place.

The upper side of a sanitary napkin generally has a liquid pervious topsheet 14. The lower side generally has a liquid impervious backsheet 16 that is joined with the topsheet 14 at the edges of the product. An absorbent core 18 is positioned between the topsheet 14 and the backsheet 16. A secondary topsheet may be provided at the top of the absorbent core 18, beneath the topsheet.

The topsheet 14, the backsheet 16, and the absorbent core 18 can be assembled in a variety of well-known configurations, including so called "tube" products or side flap products, such as, for example, configurations are described generally in U.S. Pat. No. 4,950,264, "Thin, Flexible Sanitary Napkin" issued to Osborn on Aug. 21, 1990, U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary Napkin With Flaps" issued to Van Tilburg on Aug. 18, 1987. Each of these patents is incorporated herein by reference.

The backsheet 16 and the topsheet 14 can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, or a crimp seal. A fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present invention can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the wearer's panties.

For the purpose of describing the invention, the important parts of the sanitary napkin 10 are the topsheet 14, the absorbent core 18, and, optionally, the secondary topsheet. Each of these components will be described in turn.

Figure 2:
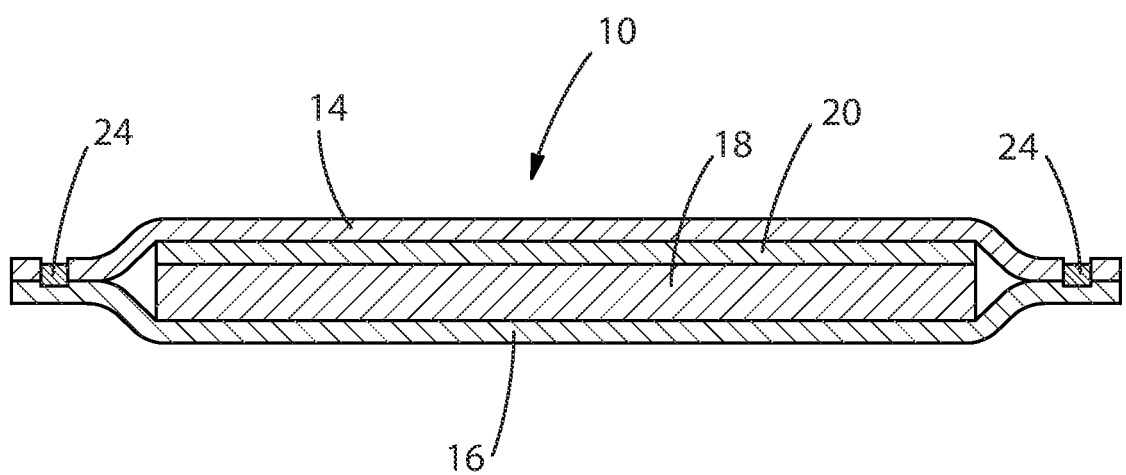
FIG. 2 is a cross-sectional view of the sanitary napkin of FIG. 1, taken through line 2-2.
Figure 3:
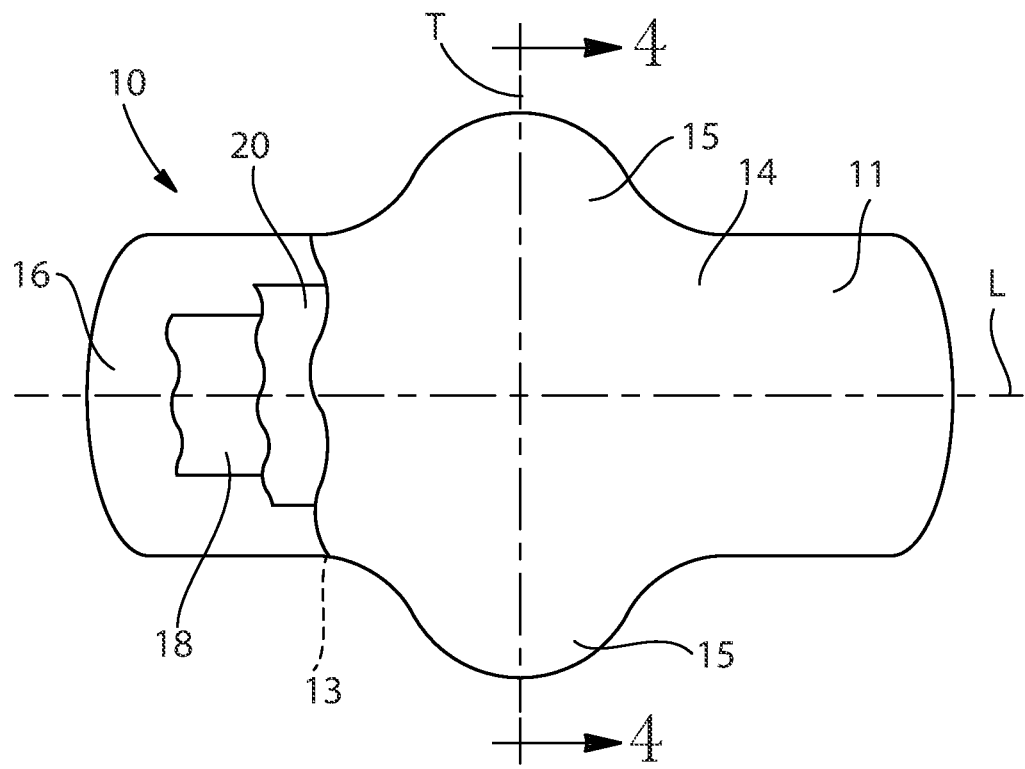
FIG. 3 is a perspective view of one embodiment of a sanitary napkin.
Figure 4:
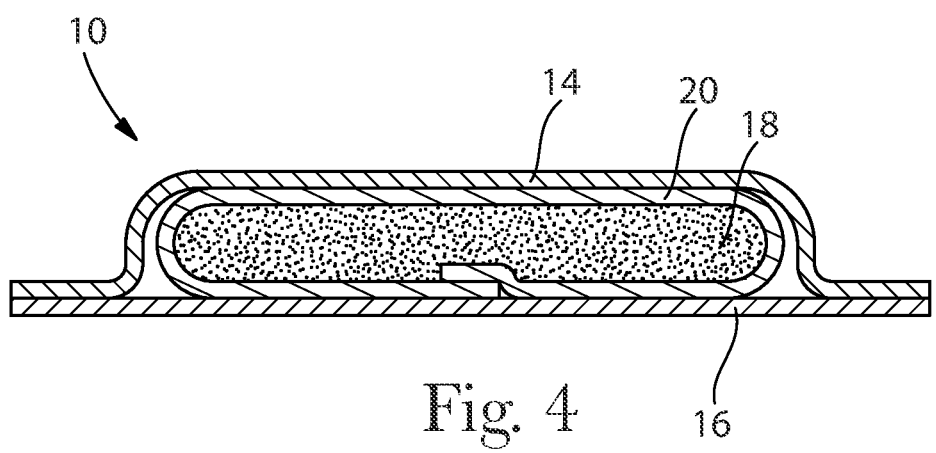
FIG. 4 is a cross-sectional view of the sanitary napkin of FIG. 1, taken through line 2-2.

The topsheet 14 is attached to bonding layer 20, such as, for example, a secondary topsheet as shown in FIG. 2. Alternatively the topsheet can be attached to bonding layer 20, which is part of absorbent core 18, as shown in FIG. 4.

Bonding Layer

The topsheet 14 is bonded to a bonding layer 20 that has a garment facing side and a wearer facing side and is formed of a fibrous matrix comprising cellulosic fibers and thermoplastic fibers. In certain embodiments, the fibrous matrix is thermally bonded, such as, for example, a thermally bonded air-laid web. The bonding layer 20 can function as a secondary topsheet or can be considered part of the absorbent core; however, the topsheet and fibrous matrix are bonded directly to each other without any intervening material or layer, such as, for example, adhesive or other material provided between the topsheet and the bonding layer 20 at the bond points. In certain embodiments, the bonding layer 20 can include additional materials on the garment facing side, such as, for example, a carrier web, but these materials will not be bonded directly to the topsheet. This provides for a softer, more comfortable, absorbent article.

In certain embodiments, the bonding layer 20 is sided, that is, the wearer facing side and the garment facing side are different. For example, the wearer facing side is typically adjacent and bonded to the topsheet and will comprise the fibrous matrix, while the garment facing side can be a material different from the fibrous matrix, such as, for example, a carrier web, such as a nonwoven, tissue, or other suitable material.

The fibrous matrix can comprise cellulosic fibers and thermoplastic fibers in any suitable amount, such as, for example, in a ratio of the basis weight of the cellulosic fibers to the basis weight of the thermoplastic fibers of from about 1.5:1, about 1.7:1, about 2:1, about 2.3:1 about 2.5:1, about 2.7:1, about 3:1, about 3.3:1, about 3.5:1, about 4:1 or more. In certain embodiments, the fibrous matrix comprises more cellulosic fibers than thermoplastic fibers.

The bonding layer can comprise cellulosic fibers and thermoplastic material, including thermoplastic fibers and/or thermoplastic powder, in any suitable amount, such as, for example, in a ratio of the basis weight of the cellulosic material to the basis weight of the thermoplastic material of greater than about 1:1, greater than about 1.1:1, or greater than about 1.5:1, such as, for example, from about 1.1:1, about 1.2:1, about 1.3:1, about 1.4:1 about 1.5:1, about 1.7:1, about 2:1, about 2.5:1, or more. In certain embodiments, the bonding layer comprises more cellulosic material than thermoplastic material.

Generally, the topsheet is bonded to the bonding layer 20 at multiple discreet bonding points, such as, for example, by pressing the topsheet into the fibrous matrix to form the bond points. In certain embodiments, the thermoplastic fibers plastically deform during the bonding process to form the bond. In addition, the fibrous matrix is able to dissipate the bonding and wear force throughout the web, decreasing the likelihood of bond destruction or breakage during bond formation or wear.

The bonding layer 20 has a fibrous web or matrix of cellulosic fibers and thermoplastic fibers. This fibrous web or matrix provides the primary medium for handling aqueous fluids and in particular discharged aqueous body fluids. This web or matrix typically provides a capillary structure for handling such fluids. In certain embodiments, the fibrous web is a bonded network of fibers, such as, for example, an air-laid web that is heated to thermally bond the fibers.

Many cellulosic materials can be used to make the web or matrix, including both naturally occurring, unmodified cellulosic fibers such as cotton, Esparto grass, bagasse, hemp, flax, wood pulp, and jute, as well as modified cellulosic fibers such chemically modified wood pulp, rayon, and the like. Such fibers can be stiffened by chemical means.

In certain embodiments, the cellulosic fibers are hydrophilic. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled Contact Angle, Wettability and Adhesion, edited by Robert F. Gould (Copyright 1964). A fiber, or surface of a fiber, is said to be wetted by a fluid (i.e., hydrophilic) when either the contact angle between the fluid and the fiber, or its surface, is less than 90.degree., or when the fluid tends to spread spontaneously across the surface of the fiber, both conditions normally co-existing. Conversely, a fiber or surface is considered to be hydrophobic if the contact angle is greater than 90.degree. and the fluid does not spread spontaneously across the surface of the fiber.

The bonding layer 20 also comprises thermoplastic material. Thermoplastic particulates or fibers can be used for this purpose. The materials, and in particular thermoplastic fibers, can be made from a variety of thermoplastic polymers including polyolefins such as polyethylene (e.g., PULPEX®) and polypropylene, polyesters, copolyesters, and copolymers of any of the foregoing.

Depending upon the desired characteristics for the resulting thermally bonded matrix, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, the term "bicomponent fibers" refers to thermoplastic fibers that comprise a core fiber made-from one polymer that is encased within a thermoplastic sheath made from a different polymer. The polymer comprising the sheath often melts at a different, typically lower, temperature than the polymer comprising the core 18. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

The length of bicomponent fibers can vary depending upon the particular properties desired for the fibers and the web formation process. Typically, in an airlaid web, these thermoplastic fibers have a length from about 2 mm to about 12 mm long, preferably from about 2.5 mm to about 7.5 mm long, and most preferably from about 3.0 mm to about 6.0 mm long. The properties—of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine can have any suitable decitex range, such as, for example, from about 1.0 to about 20 decitex, from about 1.4 to about 10 decitex, from about 1.7 to about 7 decitex, or from about 2 to about 10 decitex, such as, for example, about 2 decitex, about 4 decitex, about 6 decitex, about 8 decitex or any other suitable decitex range.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

In certain embodiments, the bonding layer 20 can also include synthetic fibers that typically do not function as binder fibers but alter the mechanical properties of the fibrous webs. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably from about 0.9 to about 1.5 cm. Suitable nonbonding thermoplastic fibers can have a decitex in the range of about 1.5 to about 35 decitex, more preferably from about 14 to about 20 decitex.

The Secondary Topsheet

In certain embodiments, the sanitary napkin 10 includes a secondary topsheet that can function as the bonding layer 20. The secondary topsheet can be interposed between the absorbent core 18 and the topsheet 14, and serves to rapidly draw discharged body fluids, in particular menstrual fluids, through the adjacent permeable (primary) topsheet 14. This allows the surface of the primary topsheet 14 adjacent the wearer of the article pad to remain relatively clean and dry.

The secondary topsheet can have any suitable basis weight, such as, for example, a basis weight of less than 125 grams per square meter, a basis weight of less than 100 grams per square meter, or a basis weight of less than 80 grams per square meter. The secondary topsheet in the illustrated sanitary napkin 10 has a basis weight of about 59 grams per square meter. It has a caliper thickness of about 0.75 mm, a density of about 0.08 grams/cubic centimeter, and a Permeability of about 80 darcy.

In the secondary topsheet used in the disclosed sanitary napkin 10, cellulosic fibers contribute about 34 grams per square meter to the basis weight of the secondary topsheet, and bicomponent fibers contribute about 10 grams per square meter to the basis weight of the secondary topsheet. In certain embodiments, the secondary topsheet can include superabsorbent material, such as, for example, fibrous superabsorbent material, such as, for example, material that is 6 mm long with a decitex of 10. Suitable material can be purchased from Technical Absorbents of the United Kingdom as Oasis type 111.

In certain embodiments, it is preferred to use less than about 3.5 grams per square meter of superabsorbent material, such as, for example, between 0.3 and 3.5 grams per square meter of superabsorbent material, more preferred to use between 0.3 and 2.5 grams per square meter of such material, and most preferred to use between 0.3 and 1.5 grams per square meter of such material. In the secondary topsheet used in the illustrated sanitary napkin, the fibrous superabsorbent material contributes 0.6 grams per square meter to the basis weight of the secondary topsheet.

The Topsheet 14

To provide for softness next to the body, the topsheet 14 of the illustrated sanitary napkin 10 is formed from a soft, smooth, flexible, porous material that is non-irritating to the user's skin. In certain embodiments, the topsheet 14 is considered soft, flimsy, and weak as compared to currently commercially available topsheets. The topsheet 14 must be permeable to the body fluids to be collected by the article and thus, for a sanitary napkin, must be permeable to vaginal discharges.

Suitable formed film topsheets for absorbent articles can be made from a wide range of materials such as apertured formed thermoplastic films, apertured plastic films, and hydroformed thermoplastic films; reticulated thermoplastic films; thermoplastic scrims; and film/nonwoven laminates. In certain embodiments, the topsheet can be hydrophobic. Hydrophobic topsheets have a reduced tendency to allow fluids to pass back through and rewet the wearer's skin. Thus, the surface of the formed film that is in contact with the body remains dry, thereby reducing body soiling and creating a more comfortable feel for the wearer.

Topsheets for use in the present invention can be hydrophobic topsheets selected from apertured 2-dimensional or 3-dimensional film topsheets. Lofty apertured formed film topsheets, with appreciable topsheet texture (nubs, microtexture or with filament-like protrusions on the body-facing surface that can trap bodily discharges and hinder low fluid flows towards the body) that may be hydrophobic or hydrophilic in nature, can also be used. Apertured formed films are especially preferred for the topsheet 14 because they are pervious to body exudates and non-absorbent.

In certain embodiments, the topsheet can be a low cost soft and silky tactile web material, such as, for example, The first web materials suitable for use in the article in accordance with an embodiment of the disclosure are advantageously lower cost materials than typical topsheet materials, such as for example, the topsheet material commercially available as the soft dry weave cover used in the ALWAYS ULTRATHIN pads (Procter & Gamble). However, such web materials tend to stick to the skin of the user during use and have low yield points, which can result in tearing of the web between bonding points when such web materials are incorporated into an absorbent article. For example, as compared to the commercially available soft dry weave cover used in the ALWAYS ULTRATHIN pads, the first web material exhibits significantly increased stick to skin and has decreased yield strength.

Suitable first web materials are described in U.S. Pat. No. 7,521,588 and U.S. Patent Publication Nos. 2010/0230857, 2010/0230858, 2010/0230866, and 2010/0230867, the disclosures of which are incorporated herein in their entireties. The first web includes a precursor web, which can include, for example, a plurality of discrete protruded extensions extending only from a first surface of the precursor web. The first web can further include macroapertures. In one embodiment, the first web includes macroapertures and does not include discrete protruded extensions.

Examples of films suitable for use as the precursor web include films of low density polyethylene (LDPE), linear low-density polyethylene (LLDPE), and blends of linear low-density polyethylene and low density polyethylene (LDPE/LLDPE). The precursor material can have a thickness of about 10 microns to about 25 microns. For example, suitable precursor web thicknesses include about 10, 11, 12, 13, 14, 15, 16, 17, 18, 19, 20, 21, 22, 23, 24, 25 microns. One material found suitable for use as the precursor web is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882).

The protruded extensions have sidewalls defining an open proximal portion and a closed distal portion. The discrete protruded elements can form hair-like fibrils that extend from a first surface of the web. The discrete protruded elements impart a soft feel to the web material, making it more desirable for use in an absorbent article, and particularly for use as a topsheet material in an absorbent article. The protruded extensions can be formed integral with the film, and can be formed by permanent local plastic deformation of film. The protruded extensions have a height measured from a minimum amplitude between adjacent protruded extensions to a maximum amplitude at the closed distal portion. The protruded extensions can have a diameter, which for a generally cylindrical structure is the outside diameter at a lateral cross-section. By "lateral" is meant generally parallel to the plane of the first surface of the web. For non-uniform lateral cross-sections, and/or non-cylindrical structures, the diameter is measured as the average lateral cross-sectional dimension at ½ the height of the protruded extension. Thus, for each protruded extensions, an aspect ratio, defined as height/diameter, can be determined. The protruded extensions can have an aspect ratio of at least 0.5. Other suitable aspect ratios include, for example, about 0.5, 1, 1.5, 2, 2.5, and 3.

The diameter of protruded extensions can remain constant or can decrease with increasing amplitude (amplitude increases to a maximum at the closed distal end). For example, the diameter, or average lateral cross-sectional dimension, of protruded extensions can be a maximum at the proximal portion and the lateral cross-sectional dimension steadily decreases to distal end. The protruded extensions can have an average cross-section diameter of about 50 microns to about 130 microns, about 60 microns to about 120 microns, about 70 microns to about 110 microns, and about 80 microns to about 100 microns. Other suitable average cross-section diameters include about 50, 60, 70, 80, 90, 100, 110, 120, and 130 microns.

The area density of the protruded extensions, which is the number of protruded extensions per unit area of the first surface of the web, can be optimized for use in absorbent articles. In general, the center-to-center spacing can be optimized for adequate tactile impression, while at the same time minimizing fiber-to-fiber entrapment of fluid. Currently, it is believed that a center-to-center spacing of about 100 microns to 250 microns is optimal for use in sanitary napkins. Minimizing entrapment of menses between fibers improves the surface cleanliness of the sanitary napkin, which, in turn improves the cleanliness and skin health of the wearer.

Figure 5:
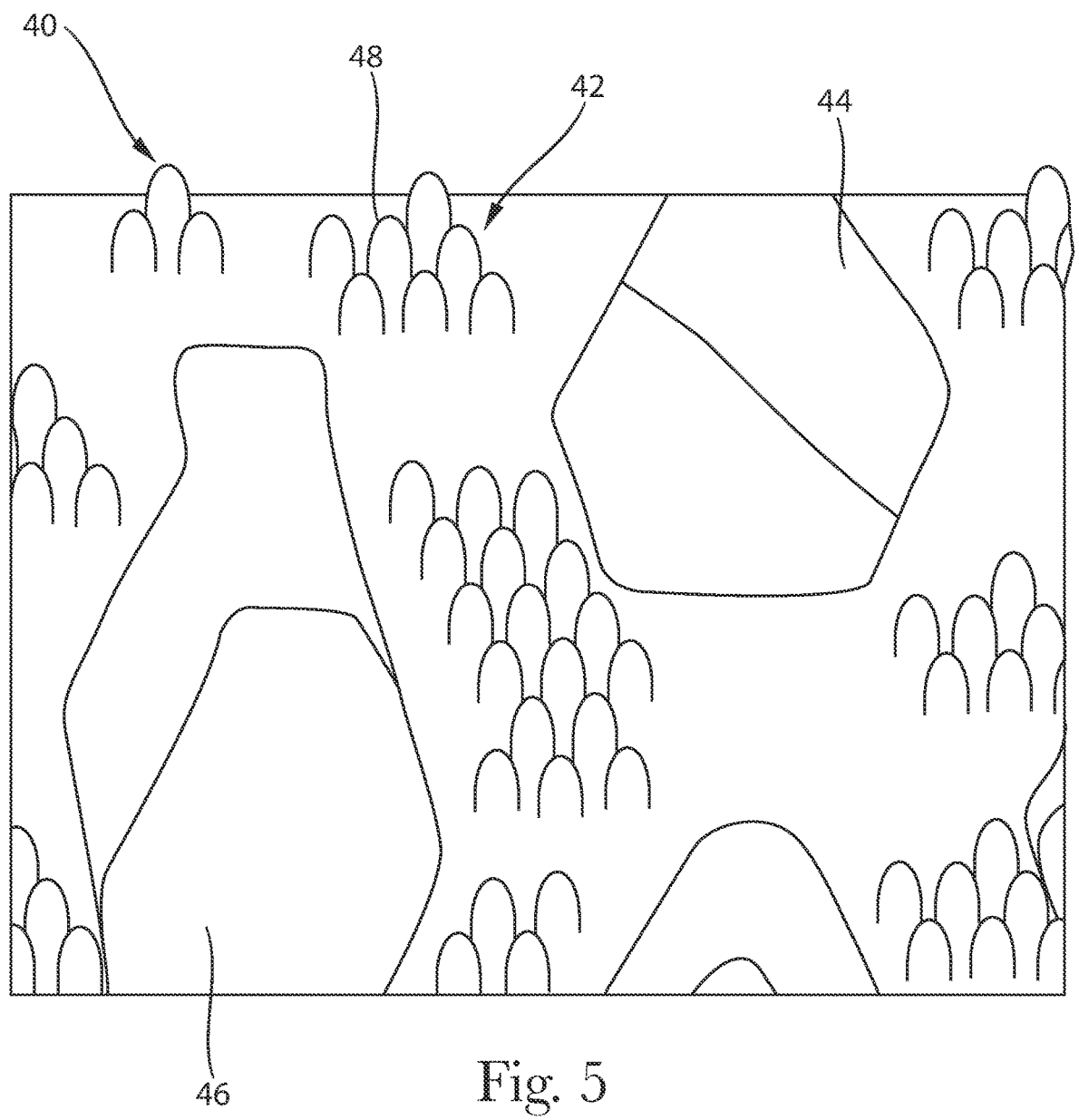
FIG. 5 is a schematic illustration of a topsheet material suitable for use in an embodiment of the disclosure.

The first web can further include a plurality of apertures to allow the first web to be liquid permeable. For example, the apertures can be macroapertures which are formed by a multiplicity of interconnecting members, such as fiber like elements, that are interconnected to one another to define a continuous first surface of the web. The macroapetures can have any suitable shape. For example, the macroapertures can polygon-shaped. In one embodiment, the macroapetures have a hexagon shape. The macroapertures can have a diameter in a range of about 300 microns to about 1000 microns, about 400 microns to about 900 microns, about 500 microns to about 800 microns, or about 600 microns to about 700 microns. In one embodiment, the first web includes macroapetures and discrete protruded extensions. The apertures can extend from the first surface of the web to a second surface of the web so as to extend in an opposite direction as the protruded extensions and the discrete protruded extensions can be disposed only the first surface of the web. Referring to FIG. 5, in one embodiment, the first web 40 can include macroapetures 46 with discrete protruded extensions 48 extending only from a top 42 (i.e., first) surface of the web. The sidewalls 44 of the macroapetures 46 remain free from discrete protruded extensions 48.

Suitable formed film topsheets are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Other aperture-formed film topsheets are disclosed in U.S. Pat. No. 4,609,518 (Curro et al), issued Sep. 2, 1986 and U.S. Pat. No. 4,629,643 (Curro et al), issued Dec. 16, 1986, which are incorporated by reference. Other suitable topsheets are disclosed in, for example, U.S. Pat. Nos. 7,172,801; 7,270,861; 7,410,683; 7,507,459; 7,553,532; 7,648,752; 7,670,665; 7,682,686; 7,718,243; and U.S. Patent Appln. Nos. 2005/0281976; 2005/0283129; 2008/0119807; 2009/0030390; 2009/0030391. One useful topsheet for the present invention is the formed film described in one or more of the above patents and marketed on sanitary napkins sold by The Procter & Gamble Company of Cincinnati, Ohio as "DRI-WEAVE."

The Absorbent Core 18

The absorbent core 18 of a sanitary napkin serves to store bodily fluids discharged during use. The core 18 can be manufactured in a wide variety of sizes and shapes, and may be profiled to have different thickness, hydrophilic gradients, superabsorbent gradients, densities, or average basis weights at different positions across the face of the product. In certain embodiments, the bonding layer 20 can be part of the absorbent core 18.

An absorbent core 18 may have a fluid distribution layer as well as a fluid storage layer. The fluid distribution layer transfers received fluid both downwardly and laterally, and generally has more permeability and less capillarity than the fluid storage layer.

In addition to conventional absorbent materials such as creped cellulose wadding, fluffed cellulose fibers, wood pulp fibers also known as airfelt, and textile fibers, the fluid storage layer often includes superabsorbent material that imbide fluids and form hydrogels. These materials are typically capable of absorbing large quantities of body fluids and retaining them under moderate pressures. The fluid storage layer of the absorbent core 18 can be made solely of superabsorbent material, or can include such materials dispersed in a suitable carrier such as cellulose fibers in the form of fluff or stiffened fibers. Synthetic fibers including cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like can also be used. The fluid storage layer can also include filler materials, such as Perlite, diatomaceous earth, Vermiculite, or other suitable materials, that lower rewet problems.

However structured, the total absorbent capacity of the absorbent core 18 should be compatible with the design loading and the intended use of the article. Thus, the size and absorbent capacity of the absorbent core 18 may be varied to accommodate different uses such as incontinence pads, pantiliners, regular sanitary napkins, or overnight sanitary napkins.

The absorbent core 18 in the illustrated sanitary napkin is made of cellulose fibers and absorbent gelling material, such as, for example, described in International Patent Application Publication No. 00/59438 (Walker), herein incorporated by reference.

The absorbent core 18 can also include other optional components sometimes used in absorbent webs. For example, a reinforcing scrim can be positioned within the respective layers, or between the respective layers, of the absorbent core 18.

The backsheet 16 that covers the lower side of the absorbent core 18 prevents the fluids in the absorbent core 18 from wetting articles that contact the sanitary napkin 20, such as pants, pajamas and undergarments. Accordingly, the backsheet 16 is preferably made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

Superabsorbent Material

Suitable absorbent gelling materials for use in the invention can comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988, both of which are incorporated by reference. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose.

Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and cross-linking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al); issued Feb. 28, 1978, which is incorporated by reference. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole per-cent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

While these absorbent gelling materials are typically in particle form, it is also contemplated that the absorbent gelling material can be in the form of macrostructures such as fibers, sheets or strips. These macrostructures are typically prepared by forming the particulate absorbent gelling material into an aggregate, treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992, which is incorporated by reference.

Formation of the Bonding Layer

The mixtures of fibers, thermoplastic material, and, optionally, superabsorbent material, can be formed into layers by any of a variety of techniques, including air-laying methods.

In certain embodiments, the bonding layer 20 can be formed by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al), issued Oct. 5, 1982; U.S. Pat. No. 4,353,687 (Hosler et al), issued Oct. 12, 1982; U.S. Pat. No. 4,494,278 (Kroyer et al), issued Jan. 22, 1985; U.S. Pat. No. 4,627,806 (Johnson), issued Dec. 9, 1986; U.S. Pat. No. 4,650,409 (Nistri et al), issued Mar. 17, 1987; and U.S. Pat. No. 4,724,980 (Farley), issued Feb. 16, 1988, all of which are incorporated by reference.

A particularly desirable system for air-laying mixtures of fibers and thermoplastic material according to the present invention is disclosed in U.S. Pat. No. 4,640,810 (Laursen et al), issued Feb. 3, 1987, which is incorporated by reference.

In certain embodiments, the bonding layer 20 can be formed as a secondary topsheet by airlaying the cellulose, thermoplastic material, and, optionally, fibrous superabsorbent material onto a nonwoven carrier, such as, for example, a nonwoven carrier made of spunbonded polyolefins, such as, for example, spunbonded polypropylene. The resulting fibrous matrix can be heated to create a bonded network of fibers within the fibrous web, such as, for example, in the form of a thermally bonded airlaid web. In addition, in certain embodiments, latex can be sprayed onto one or both sides of the bonding layer 20.

There are different ways to combine the bonding layer 20 and the absorbent core 18. The bonding layer 20 can be formed separately from the absorbent core 18 and then combined later after thermal bonding/densification. Alternatively, the bonding layer 20 and all or parts of the absorbent core can be formed together or on top of the other.

Bonding

The topsheet and bonding layer 20 can be joined in any suitable manner or configuration. In certain embodiments, the topsheet and bonding layer 20 can be joined by a plurality of discrete bonding points that can be formed by any known means. For example, the bonding points can be formed by melt fusing the topsheet and the bonding layer 20 at discrete bonding points. Suitable examples of methods of bonding can be found in U.S. Pat. Nos. 7,056,404 and 4,854,984. In certain embodiments, the bonding points are adhesive-free, that is, no adhesive is provided between the topsheet and bonding layer 20.

The topsheet and bonding layer 20 can be joined in any suitable pattern. In certain embodiments, the bonding pattern can adhere together at least one of the first end regions of the topsheet and bonding layer 20 and/or the second end regions of the topsheet and bonding layer 20. In certain embodiments, the bonding patterning can include a sized spacing between adjacent bonding points sufficient to have inscribed therein a circle having a diameter of about 1 mm to about 12 mm. The circle can be inscribed so as to be tangent to the adjacent bonding points. Other suitable diameters include about 2 mm to about 10 mm, about 3 mm to about 10 mm, and about 4 mm to about 8 mm. For example, the sized spacing can be sufficient to have inscribed therein a circle having a diameter of about 1 mm, 2 mm, 3 mm, 4 mm, 5 mm, 6 mm, 7 mm, 8 mm, 9 mm, 10 mm, 11 mm, and 12 mm. As used herein, "adjacent bonding points" refers to two bonding points, which can be connected by a straight line that does not intersect or otherwise touch another bonding point. Adjacent bonding points are also disposed in the same end region (the first end region or the second end region).

The bonding pattern can cover about 10% to about 20%, about 15% to about 20%, about 12% to about 18%, or about 14% to about 16% of the total surface area of the first or second end regions 10 and 12, respectively, of the first and second webs. For example, the bonding pattern 18 can cover about 10%, 11%, 12%, 13%, 14%, 15%, 16%, 17%, 18%, 19%, or 20% of the total surface area of the first and second end regions, respectively.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a liquid pervious film topsheet having a body facing surface and a garment facing surface,
   wherein the liquid pervious film topsheet comprises a plurality of discrete protruded extensions and a plurality of macroapertures,
   wherein the plurality of discrete protruded extensions extends from the body facing surface of the liquid pervious film topsheet in a direction away from the garment facing surface,
   wherein the plurality of discrete protruded extensions have a center-to-center spacing of about 100 microns to 250 microns, and
   wherein the plurality of macroapertures have a diameter in a range of about 300 microns to about 1000 microns;
   a backsheet having a body facing surface and a garment facing surface;
   an absorbent core having a body facing surface and a garment facing surface, the absorbent core being provided between the topsheet and the backsheet; and
   a bonding layer having a body facing surface and a garment facing surface, the body facing surface of the bonding layer having a fibrous matrix comprising thermoplastic fibers, wherein the garment facing surface of the topsheet is directly bonded to the body facing surface of the bonding layer at discrete adhesive-free bond points,
   wherein the discrete bond points covers at least about 10% to about 20% of a surface area of the absorbent article,
   wherein the discrete bond points have a sized spacing between adjacent bonding points sufficient to have inscribed therein a circle having a diameter of about 1 mm to about 12 mm; and
   wherein a majority of the discrete bond points have an area less than 2.5 square millimeters.

2. The absorbent article of claim 1, wherein the fibrous matrix comprises cellulosic fibers, and wherein the ratio of the basis weight of the cellulosic fibers to the basis weight of the thermoplastic fibers is greater than about 1:1.

3. The absorbent article of claim 1, wherein the bonding layer is part of the absorbent core.

4. The absorbent article of claim 1, wherein the thermoplastic fibers are bicomponent fibers.

5. The absorbent article of claim 4, wherein the bicomponent fibers are from about 2 to about 10 decitex.

6. The absorbent article of claim 1, wherein the topsheet and the bonding layer are bonded together using melt fusion bonding.

7. The absorbent article of claim 1, wherein the absorbent article is a sanitary napkin or pantyliner.

8. An absorbent article comprising:
   a liquid pervious film topsheet having a body facing surface and a garment facing surface,
   wherein the liquid pervious film topsheet comprises a plurality of discrete protruded extensions and a plurality of macroapertures,
   wherein the plurality of discrete protruded extensions extends from the body facing surface of the liquid pervious film topsheet in a direction away from the garment facing surface,
   wherein the plurality of macroapertures have a diameter in a range of about 300 microns to about 1000 microns;
   a backsheet having a body facing surface and a garment facing surface;
   an absorbent core having a body facing surface and a garment facing surface, the absorbent core being provided between the topsheet and the backsheet; and
   a bonding layer having a body facing surface and a garment facing surface, the body facing surface of the bonding layer having a fibrous matrix comprising thermoplastic fibers and the garment facing surface of the bonding layer being different from the body facing surface of the bonding layer, wherein the garment facing surface of the topsheet is directly bonded to the body facing surface of the bonding layer at discrete bond points forming a bond pattern,
   wherein the bond pattern covers at least about 10% to about 20% of a surface area of the absorbent article,
   wherein the bond pattern has a sized spacing between adjacent bonding points sufficient to have inscribed therein a circle having a diameter of about 1 mm to about 12 mm; and
   wherein a majority of the discrete bonds of the bond pattern have an area less than 2.5 square millimeters.

9. The absorbent article of claim 8, wherein the fibrous matrix comprises cellulosic fibers, and wherein the ratio of the basis weight of the cellulosic fibers to the basis weight of the thermoplastic fibers is greater than about 1:1.

10. The absorbent article of claim 8, wherein the garment facing surface of the bonding layer comprises a carrier web.

11. The absorbent article of claim 8, wherein the thermoplastic fibers are bicomponent fibers.

12. The absorbent article of claim 8, wherein the bond points are adhesive-free.

13. The absorbent article of claim 8, wherein the topsheet and the bonding layer are bonded together using melt fusion bonding.

14. An absorbent article comprising:
a liquid pervious film topsheet having a body facing surface and a garment facing surface, the topsheet comprising a plurality of discrete protruded extensions and macroapertures, wherein the plurality of discrete protruded extensions extends from the body facing surface of the liquid pervious film topsheet in a direction away from the garment facing surface;
a backsheet having a body facing surface and a garment facing surface;
an absorbent core having a body facing surface and a garment facing surface that is provided between the topsheet and the backsheet; and
a bonding layer having a body facing surface and a garment facing surface, the body facing surface of the bonding layer having a fibrous matrix comprising thermoplastic fibers, wherein the garment facing surface of the topsheet is directly bonded to the body facing surface of the bonding layer at discrete bond adhesive-free bond points,
wherein the discrete bond points covers at least about 10% to about 20% of a surface area of the absorbent article,
wherein the discrete bond points have a sized spacing between adjacent bonding points sufficient to have inscribed therein a circle having a diameter of about 1 mm to about 12 mm; and
wherein a majority of the discrete bond points have an area less than 2.5 square millimeters.

15. The absorbent article of claim 14, wherein the fibrous matrix comprises cellulosic fibers, and wherein the ratio of the basis weight of the cellulosic fibers to the basis weight of the thermoplastic fibers is greater than about 1:1.

16. The absorbent article of claim 15, wherein the ratio of the basis weight of the cellulosic fibers to the basis weight of the thermoplastic fibers is from about 1:1 to about 4:1.

17. The absorbent article of claim 14, wherein the thermoplastic fibers are bicomponent fibers.

18. The absorbent article of claim 17, wherein the bicomponent fibers are from about 2 to about 10 decitex.

19. The absorbent article of claim 18, wherein the topsheet and the bonding layer are bonded together using melt fusion bonding.

20. The absorbent article of claim 14, wherein the garment facing surface of the bonding layer comprises a carrier web.

* * * * *